United States Patent [19]
Kawai et al.

[11] Patent Number: 5,849,282
[45] Date of Patent: Dec. 15, 1998

[54] METHOD OF TREATING COLON, RENAL, AND LUNG CARCINOMAS WITH γ-INTERFERON AND [SER$^{71}$]-INTERLEUKIN-1β

[75] Inventors: Kazuyoshi Kawai; Yasue Konishi; Satoru Nakai, all of Itano-gun; Yoshikatsu Hirai, Suita, all of Japan

[73] Assignee: Otsuka Pharmaceutical Co., Ltd., Tokyo, Japan

[21] Appl. No.: 173,866

[22] Filed: Dec. 23, 1993

Related U.S. Application Data

[63] Continuation of Ser. No. 778,917, Dec. 31, 1991, abandoned.

[30] Foreign Application Priority Data

May 9, 1990 [JP] Japan .................................. 2-120557

[51] Int. Cl.$^6$ .................. A61K 45/05; A61K 37/66; C07K 14/545; C07K 14/57
[52] U.S. Cl. .................. 424/85.1; 424/85.2; 424/85.4; 424/85.5; 530/351
[58] Field of Search .................. 530/351; 435/69.5, 435/69.51, 69.52; 424/85.1, 85.2, 85.3, 85.5; 574/12

[56] References Cited

U.S. PATENT DOCUMENTS

| | | | |
|---|---|---|---|
| 4,898,818 | 2/1990 | Nakai et al. ......................... | 435/69.1 |
| 5,145,667 | 9/1992 | von Eichborn et al. ............... | 424/85.5 |
| 5,145,677 | 9/1992 | von Eichborn et al. ............... | 424/85.5 |

FOREIGN PATENT DOCUMENTS

| | | |
|---|---|---|
| 0149551 | 7/1985 | European Pat. Off. . |
| 0181455 | 9/1985 | European Pat. Off. . |
| 0241242 | 10/1987 | European Pat. Off. . |
| 55-98118 | 7/1980 | Japan . |
| 59-95220 | 6/1984 | Japan . |
| 60-226820 | 11/1985 | Japan . |
| 61-277628 | 12/1986 | Japan . |
| 61-280432 | 12/1986 | Japan . |
| 62-265233 | 11/1987 | Japan . |

OTHER PUBLICATIONS

Momparler, "In vitro Systems for Evaluation of Combination Chemotherapy", *Pharmac. Ther.*, 8:21–35 (1980).
Dempsey et al, "The Differential Effects of Human Leukocytic Pyrogen/Lymphocyte–Activating Factor, T Cell Growth Factor, and Interferon on Human Natural Killer Activity", *J. Immuno.*, 129(6):2504–2510 (1982).
Tsai et al, "Modulation of Cell Proliferation by Human Recombinant Interleukin–1 and Immune Interferon", *J.N.C.I.*, 79(1):77–81 (1987).
Chen et al, "Interferon–γ Synergizes with Tumor Necrosis Factor and with Interleukin 1 and Requires the Presence of Both Monokines to Induce Antitumor Cytotoxic Activity in Macrophages", *J. Immuno.*, 139(12):4096–4101 (1987).
Hashimoto et al, "Role of Culture Supernatant of Cytotoxic/Cytostatic Macrophages in Activation of Murine Resident Peritoneal Macrophages", *Canc. Immuno. Immunotherapy*, 28(4):253–259 (1989).
Sodhi et al, "Activation of Murine Macrophages by Tumor Necrosis Factor, Interleukin–1, Interferon–γ and Cisplatin", *Immuno. Letters*, 26(1):45–50 (1990).
Kurtz et al, "Separate and Combined Effects of Recombinant Interleukin–1α and Gamma Interferon on Antibacterial Resistance", *Infect. Immuno.*, 57(2):553–558 (1989).
Kamogashira et al. 1988. Biochem Biophys Res. Commun. 150(3): 1106–1114.
Wheelock, *Science*, 149:310–311 (1965).
Falcoff, *J. Gen. Virol.*, 16:251–253 (1972).
Yip et al, *Science*, 215:411–413 (1982).
Crane et al, *J. Nat'l Cancer Inst.*, 61:871–874 (1978).
Blalock et al, *Cell Immunol.*, 49:390–394 (1980).
Mizel, *Immunol. Rev.*, 63:51–71 (1982).
Dinarello, *New Engl. J. Med.*, 311:1413–1418 (1984).
Falkoff et al, *J. Immunol.*, 131:801=805 (1983).
Onozaki et al, *J. Immunol.*, 135:3962–3968 (1985).
Romano et al, *Proc. ACCR*, 27:316 (1986).
Perez et al, *Proc. ASCO*, 5:234 (1986).
Nathan et al, *Nature*, 292:842–843 (1981).
Matsuyama et al, *J. Immunol.*, 129:450–451 (1982).
Gray et al, *Nature*, 295:503–508 (1982).
Rinderknecht et al, *J. Biol. Chem.*, 259:6790–6797 (1984).
Semple et al, *Cancer Res.*, 38:1345–1355 (1978).
Moore et al, *J. Am. Med. Assoc.*, 199:519–524 (1967).
Leibovitz et al, *Cancer Res.*, 36:4562–4569 (1976).
Leibovitz, *Am. J. Hyg.*, 78:173–180 (1963).
Fogh et al, *J. Nat'l Cancer Inst.*, 58:209–214 (1977).
Eagle, *Science*, 130:432–437 (1959).
North et al. 1988 J. Exp. Med. 168 : 2031.
Krigel et al 1987. AAOHN J. 35(4) : 159.
Onozaki et al 1985 J. Immunol 135(6): 3962.

*Primary Examiner*—Karen Cochrane Carlson
*Attorney, Agent, or Firm*—Sughrue, Mion, Zinn, Macpeak & Seas, PLLC

[57] ABSTRACT

This invention provides an anti-tumor agent and a method for treating a tumor wherein gamma-interferon and interleukin-1 are used as active ingredients.

2 Claims, No Drawings

METHOD OF TREATING COLON, RENAL, AND LUNG CARCINOMAS WITH γ-INTERFERON AND [SER$^{71}$]-INTERLEUKIN-1β

This is a Continuation of application Ser. No. 07/778,917, filed Dec. 31, 1991, now abandoned.

TECHNICAL FIELD

The present invention relates to a pharmaceutical composition comprising gamma-interferon and interleukin-1.

BACKGROUND ART

Gamma-interferon was first discovered in 1965 when E. F. Wheelock [Science, 149, 310–311, 1965] found that cultivation of human leukocytes in the presence of PHA (phytohemagglutin) as an inducer produces a virus inhibition factor which is inactivated at pH 2. R. Falcoff [J. Gen. Virol., 16, 251–253, 1972] then reported that the virus inhibition factor, which is inactivated at pH 2, is a substance having a molecular weight of 50000. Thereafter, Y. K. Yip et al. [Science, 215, 411–413, 1982] reported that when subjected to SDS-polyacrylamide gel electrophoresis (SDS-PAGE), gamma-interferon is separated into a fraction having a molecular weight of 25000 and a fraction having a molecular weight of 20000. Meanwhile, it is known that gamma-interferon has not only antiviral activity but also antitumor activity, with J. L. Crane et al. [J. L. Crane, L. A. Glasgow, E. R. Kern, and J. S. Younger, J. Natl. Cancer Inst., 61, 871–874, 1978] and J. E. Blalock et al. [J. E. Blalock, J. A. Georgiades, M. P. Langford and H. M. Johnson, Cell Immunol., 49, 390–394, 1980] reporting that the antitumor activity of gamma-interferon is 20 to 100 times as high as those of alpha- and beta-interferons.

On the other hand, interleukin-1 is a polypeptide having a molecular weight of about 12000 to 18000, which is produced from the monocytes or macrophages activated by a lipopolysaccharide or the like [S. B. Mizel, Immunol. Rev., 63, 51–71, 1982]. Interleukin-1 is not only associated with the activation of T-cells but also performs a diversity of functions in the living body [C. A. Dinarello, New Eng. J. Med., 311, 1413–1418, 1984]. For example, as it was once called B cell activating factor, interleukin-1 acts on B-cells and, in cooperation with B cell differentiation factor (BCDF), induces the production of immunoglobulin [R. J. Falkof, A. Muraguchi, J. X, Hong, et al., J. Immunol., 131, 801–805, 1983]. In addition, interleukin-1 acts on various other cells to display a variety of biological activities, and plays major roles in almost all biological reactions such as immunity, inflammation, hematopoiesis, endocrine and cerebroneural functions and so on. Furthermore, interleukin-1 exhibits direct growth-inhibitory or cytocidal effects on various kinds of tumor cells [K. Onozaki, K. Matsushima, B. B. Aggarwal, et al., J. Immunol., 135, 3962, 1985] and, as such, is expected to be of value as an antitumor agent.

Thus, both gamma-interferon and interleukin-1 have growth-inhibitory effects on tumor cells but in clinical studies using antitumor compositions containing either one of them as the active ingredient, a variety of side effects such as pyrexia, gastrointestinal symptoms, general malaise, hypotension, muscleache, etc. have been reported [H. A. Harvey, A. Lipton, D. S. Wlite, et al., Proc. ASCO, 24, 46, 1983]. Therefore, despite the efficacy for cancer therapy expected of both gamma-interferon and interleukin-1, the idea of administration thereof in high doses or the like is forced to be abandoned due to such side effects.

The object of the present invention is to provide an antitumor composition which insures a potentiated antitumor activity of gamma-interferon or interleukin-1 to thereby help reduce the dosage and, hence, the risk of side effects.

DISCLOSURE OF THE INVENTION

In the course of our research in an attempt to accomplish the above object, we conducted a screening of substances which would potentiate the antitumor activity of gamma-interferon or interleukin-1 but no satisfactory results could be obtained. Surprisingly, however, when gamma-interferon and interleukin-1 were used in combination, it was found that their antitumor activities were synergistically potentiated so much that a sufficient tumor growth-inhibitory effect could be obtained even at low doses at which neither of the drugs, used alone, show any antitumor effect, thus allowing it to markedly reduce the dosage of the drugs. The present invention is predicated on the above finding.

The present invention provides an antitumor composition containing gamma-interferon and interleukin-1 as active ingredients.

In a further aspect, the present invention provides a method of treating a tumor which comprises administering an anti-tumor effective amount of gamma-interferon and interleukin-1 to a tumor-bearing patient.

The gamma-interferon to be used in the antitumor composition of the present invention may be any of natural gamma-interferons, recombinant gamma-interferons and the derivatives thereof so far as they have a gamma-interferon activity, particularly human gamma-interferon activity. The general procedure for production of gamma-interferon, in the case of a natural interferon, comprises isolating human leukocytes or culturing human cells to obtain a T-cell line and inducing the production using an inducer such as PHA, ConA or the like [Ilana Nathan et al., Nature, 292, 842, 1981; Masako Matsuyama et al., The Journal of Immunology, 129, 450, 1982]. However, since large-scale production of cells by this method involves many difficulties in terms of technology and cost, a hamster method has been developed (Japanese Examined Patent Publication No. 63-1296 and No. 56-54158). The method may be summarized as follows. Using a young hamster previously dosed with an immunosuppresent, a T-cell line is subcutaneously transplanted at the back and allowed to grow, whereupon a tumor mass is formed in the hamster back. When the mass has reached a certain size, it is excised, cut and disrupted to provide a cell suspension. To the T-cells thus prepared, PHA is added to induce the production of gamma-interferon. The gamma-interferon produced in this manner is characterized by having a sugar chain which is identical to that of natural gamma-interferon. An alternative method for the stable and inexpensive production of gamma-interferon comprises growing a microorganism into which a human gamma-interferon gene has been introduced by a gene recombination method [Patrik W. Gray et al., Nature, 295, 501, 1982]. However, the gamma-interferon produced by this method has no sugar chain [Ernst Rinderknecht et al., The Journal of Biological Chemistry, 259, 6790, 1984].

Among the above gamma-interferons, the one produced by the hamster method is preferred.

On the other hand, interleukin-1 to be used in the present invention includes, among others, various natural, recombinant interleukin-1 or derivatives thereof which have interleukin-1 activity, particularly human interleukin-1 activity. A natural interleukin-1 can be produced by the method described in Japanese Unexamined Patent Publication No. 62-174022. A variety of recombinant interleukins-1 or derivatives thereof can be produced by the methods described in Japanese Unexamined Patent Publication No. 63-152398 and European Patent Publication EP 0237967A2, for instance.

Among such interleukin-1, there may be mentioned IL-1β as such or interleukin-1β derivatives as disclosed in the above-mentioned Japanese Unexamined Patent Publication No. 63-152398 and European Patent Publication EP 0237967A2, such as those listed below.

IL-1β as such

[Gly$^4$]IL-1β (IL-1β wherein Arg in position-4 is replaced by Gly)

[Ser$^{71}$]IL-1β (IL-1β wherein Cys in position-71 is replaced by Ser)

[Ala$^8$]IL-1β (IL-1β wherein Cys in position-8 is replaced by Ala)

[Ala$^{71}$]IL-1β (IL-1β wherein Cys in position-71 is replaced by Ala)

[Leu$^{93}$]IL-1β (IL-1β wherein Lys in position-93 is replaced by Leu)

[Arg$^{120}$]IL-1β (IL-1β wherein Trp in position-120 is replaced by Arg)

[Tyr$^{30}$]IL-1β (IL-1β wherein His in position-30 is replaced by Tyr)

[Ala$^8$Ala$^{71}$]IL-1β (IL-1β wherein Cys in position-8 is replaced by 8-position Ala and Cys in position 71 is replaced by 71-position Ala)

IL-1β-(4–153)polypeptide (IL-1β which is deficient in the amino acid sequence from Ala at 1-position to Val at 3-position).

IL-1β-(1–150)polypeptide (IL-1β wherein the amino acids at 151-position et seq. are deficient)

It should be understood that the above IL-1β and IL-1β derivatives are described with reference to amino acid sequence mentioned for interleukin-1β in Japanese Unexamined Patent Publication No. 63-152398 and European Patent Publication EP 0237967A2 referred to hereinbefore.

The antitumor composition of the present invention can be administered in the form of a single preparation containing both gamma-interferon and interleukin-1 or can be administered in the form of two preparations for separate doses, one containing gamma-interferon and the other containing interleukin-1. In whichever case, gamma-interferon and interleukin-1 potentiate the tumor cell growth inhibitory activity of each other and, therefore, the ratio of the two ingredients can be chosen from an extremely broad range.

For clinical application of the antitumor composition of the invention, the effective daily dose for human adults can be selected from a broad range. Thus, for human adults, gamma-interferon can generally be used in the range of about 4.2 μg/body to 4.2 mg/body per day and interleukin-1 can be used preferably in the range of about 0.08 to 8 μg/body per day. In the composition of the present invention, gamma-interferon and interleukin-1 potentiate the tumor cell growth inhibitory activity of each other, as mentioned hereinbefore. Therefore, when gamma-interferon is used in the clinical dose generally recommended in this field, the usual clinical dose of interleukin-1 can be reduced to about one-hundredth (1/100) to about nine-tenths (9/10). Similarly, when interleukin-1 is used in the clinical dose generally recommended in this field, the usual clinical dosage of gamma-interferon can be reduced to about one-hundredth (1/100) to about nine-tenths (9/10). From the standpoint of avoiding the aforesaid risk of side effects, it is preferable to use either gamma-interferon or interleukin-1 in a low dose within the above-mentioned effective range.

The antitumor composition of the present invention can be used in a variety of dosage forms commonly employed in the field according to intended uses. Particularly, in the manufacture of the antitumor composition of the present invention, the stability of the active ingredients, particularly of interleukin-1, can be better insured by incorporating at least one member selected from the group consisting of human serum albumin, sugars and surfactants.

The sugars mentioned above are not particularly limited and include, for example, monosaccharides such as glucose, mannose, galactose, fructose, etc., sugar alcohols such as mannitol, inositol, xylytol, etc., disaccharides such as sucrose, maltose, lactose, etc., and polysaccharides such as dextran, hydroxypropylstarch and so on. These sugars can be used alone or in combination. Particularly preferred sugars are sucrose, maltose, mannitol, inositol and dextran.

The surfactants mentioned above are not particularly limited, either. Thus, both ionic and nonionic surfactants can be useful. Preferred surfactants are polyoxyethylene glycol sorbitan alkyl esters, polyoxyethylene alkyl ethers, sorbitan monoacyl esters, fatty acid glycerides and so on.

The amount of said sugar to be used is not less than about 0.1 mg, preferably about 1 to 100 mg, per μg of interleukin-1 or a derivative thereof (hereinafter collectively referred to as "IL-1 active substance"). The amount of said surfactant to be used is not less than about 0.0001 mg, preferably about 0.001 to 0.1 mg, per μg of the IL-1 active substance. The amount of human serum albumin to be used per μg of an IL-1 active substance is not less than about 0.001 mg and preferably about 0.01 to 10 mg.

The antitumor composition of the present invention can be provided in a variety of dosage forms which are generally used for administration of drugs of this kind and, thus, may contain other pharmacologically active substances and/or conventional pharmaceutical excipients and other additives.

Particularly in regard to other ingredients which can be incorporated in the antitumor composition of the present invention, a conventional sulfur-containing reducing agent can be mentioned for further improving the stability of the IL-1 active substance. The preferred sulfur-containing reducing agent includes, for example, such relatively mild reducing agents as cysteine, N-acetylhomocysteine, thioctic acid and thioglycolic acid, and salts thereof, thioethanolamine, thioglycerol, sodium thiosulfate, thiolactic acid, dithiothreitol, glutathione and so on. These reducing agents may be used alone or in combination. The amount of such reducing agent or agents to be used (a combined amount if more than one species is used) is not critical but is appropriately not less than about 0.001 mg, preferably about 0.01 to 10 mg, per μg of the IL-1β active substance.

The antitumor composition of the present invention is preferably made isotonic with a suitable buffer to give a stable isotonic preparation. Typical buffer to be used includes various buffer solutions having a pH of about 4 to 8, preferably about 5 to 6, such as citric acid-sodium citrate, citric acid-sodium phosphate, acetic acid-sodium acetate, citric acid-borax and so on.

The antitumor composition of the present invention may be provided, for example, as a pharmaceutical preparation containing pharmacologically effective amounts of gamma-interferon, IL-1 active substance and other ingredients mentioned above in combination with pharmaceutically acceptable vehicles. Thus, according to the kinds of preparations to be used, there can be employed, as such vehicles, any of those excipients and diluents, e.g. fillers, volume builders, binders, humectants, disintegrating agents, etc., which are commonly used in pharmaceutical manufacturing. There is no particular limitation on the dosage form that can be used so far as it can effectively contain the active ingredients. Thus, solid forms such as tablets, powders, granules, pills as well as injectable liquid forms such as solutions, suspensions, emulsions, etc. can be adopted. The antitumor composition of the invention may also be in a dry form which can be reconstituted into a liquid form by addition of an appropriate vehicle prior to use. Any of the above-mentioned preparations can be manufactured by conventional procedures.

These pharmaceutical preparations can be administered by an appropriate route. For example, injectable preparations can be administered intravenously, intramuscularly, subcutaneously, intradermally or intraperitoneally, and solid preparations can be administered orally or per rectum. The administration may be made in a single dose a day or in 3 to 4 divided doses a day.

According to the present invention, when gamma-interferon and interleukin-1 are used conjointly, each of them mutually potentiates the antitumor activity so that a sufficient tumor growth-inhibitory effect can be obtained even at a low dosage level where neither of the drugs, used alone, is effective. As a consequence, drastic dosage reduction for both drugs and, hence, reduction of risk levels for various side effects can be realized.

EXAMPLES

Reference Example 1

Preparation of gamma-interferon

A gamma-interferon was prepared in accordance with the method described in Japanese Examined Patent Publication No. 63-1296 (Jan. 12, 1988), as follows.
(1) Growing the cells BALL-1 cells were grown in RPMI-1640 medium (pH 7.2) containing 20% of FCS (fetal calf serum) at 37° C. The resulting cells were washed with serum-free RPMI-1640 medium (pH 7.2) and suspended in the same medium to give a concentration of about $1 \times 10^6$ cells/ml.

The BALL-1 cells prepared above were transplanted subcutaneously into newborn hamsters which had been immunosuppressed by administration of rabbit antiserum, and the animals were bred in the usual manner for about 3 weeks. Then, the mass of BALL-1 cells grown beneath the skin was excised, finely divided and suspended in trypsin-containing physiological saline to give a cell suspension.

The cells were washed with serum-free RPMI-1640 medium and suspended in the same medium containing 10% FCS to give a concentration of about $1 \times 10^6$ cells/ml. The resulting suspension was used in the following production of gamma-interferon.
(2) Production of gamma-interferon To the suspension of BALL-1 cells in RPMI-1640 medium containing 10% FCS prepared by the procedure of (1) above, 100 ng of lipopolysaccharide (LPS) was added as an inducing agent and the mixture was incubated at 37° C. for 3 days to induce the production of gamma-interferon.

After incubation, the system was centrifuged to remove the cells and the supernatant was concentrated by ultrafiltration. The concentrate was then purified using a monoclonal antibody column. The specific activity of this product was $7.35 \times 10^6$ IU/mg protein.

Reference Example 2

Preparation of interleukin-1

In accordance with the method described in Example 1 of Japanese Unexamined Patent Publication No. 63-152398, an interleukin-1β wherein Cys in position-71 is replaced by Ser was prepared, isolated and purified.

Then, using the gamma-interferon obtained in Reference Example 1 and the interleukin-1 obtained in the above Reference Example 2 in various ratios, the growth inhibitory effect on tumor cells was evaluated. The results are set forth hereafter in Examples 1 (1) through (3).

Example 1

Combined inhibitory effect on growth of human tumor cell lines (1) Effect on COLO 205 cells COLO 205 cells (human colon carcinoma cell, Cancer Res., 38, 1345, 1978) were cultured in accordance with the method of Moore et al. (J. Am. Med. Assoc., 199, 519, 1967) and the resulting cells were washed twice with PBS (−) solution (Nissui Pharmaceutical, phosphate-buffered physiological saline). Following detachment of the cells with 0.05% trypsin (Flow Laboratories), the cells were pipetted into RPMI-1640 medium (GIBCO Laboratories) to provide a cell suspension. The cells were centrifugally washed at 1200 rpm (25° C.) for 5 minutes (using Hitachi 05PR-22), and resuspended in the same medium, followed by addition of FBS (fetal bovine serum, GIBCO Laboratories) to a final concentration of 10%. After staining the cells with trypan blue solution (Wako Pure Chemicals), the number of viable cells were counted under a light microscope.

Using a 12-well microtiter plate (Costar), cell suspensions in a dilution series from $6.3 \times 10^2$ cells/ml to $2 \times 10^4$ cells/ml were placed, in 0.5 ml portions, in the wells and incubated under 5% $CO_2$ at 37° C. for 9 days (Napco $CO_2$ incubator) for a preliminary analysis of cell concentration and incubation time. Then, 0, 0.014, 0.14, 1.4, 14 or 140 ng/ml (i.e. 0, 0.1, 1, 10, 100 or 1000 u/ml) of the gamma-interferon of Reference Example 1 (hereinafter referred to as IFN-γ) and 0, 0.01, 0.1, 1, 10 or 100 ng/ml of the interleukin-1β of Reference Example 2 (hereinafter referred to as IL-1β), in portions of 0.025 ml, were added in various combinations. In addition, 0.5 ml portions of a cell suspension previously adjusted to a concentration of $1.3 \times 10^3$ cells/ml according to the results of said preliminary analysis were added. The microtiter plate was then incubated under 5% $CO_2$ at 37° C. for 8 days. After the incubation, the cells in the wells were then washed with PBS (+) solution (Nissui Pharmaceutical) and fixed with methanol (Wako Pure Chemicals). After drying in the air, the cells were stained with Giemsa stain (MERCK) and the number of colonies was counted using an automatic particle counter (CP-2000, Shiraimatsu Kikai) or a stereoscopic microscope (SZH, Olympus). The rate of cell growth in each group was calculated using as control the group treated with the medium alone, in lieu of gamma-interferon and interleukin-1β. The results are set forth in Table 1.

As shown in Table 1, the growth inhibitory effect of interleukin-1β, used alone, on COLO 205 cells was weak over the concentration range of 1 ng/ml to 100 ng/ml, with only about 35% inhibition being obtained at 100 ng/ml. With the gamma-interferon alone, 65% growth inhibition was found in the 0.14 ng/ml group.

On the other hand, in the group treated with IFN-γ alone, the $ED_{50}$ value (determined by the probit method; the same applies hereinafter) of IFN-γ was 0.18 ng/ml. In contrast, in the group wherein 0.01 ng/ml of IL-1β was conjointly used, the $ED_{50}$ value of IFN-γ was 0.042 ng/ml and that in the group wherein 0.1 ng/ml of IL-1β was conjointly used was 0.007 ng/ml. Thus, a potentiation of growth inhibitory activity by as much as 4.3 to 25.7 times was obtained.

microscope (SZH, Olympus). The rate of cell growth in each group was calculated using as control the group treated with the medium alone in lieu of gamma-interferon and interleukin-1β. The results are set forth in Table 2.

TABLE 1

| IL-1β | Growth of COLO 205 cells (%) | | | | | |
|---|---|---|---|---|---|---|
| | IFN-γ (ng/ml) | | | | | |
| (ng/ml) | 0 | 0.014 | 0.14 | 1.4 | 14 | 140 |
| 0 | 100.0 ± 2.9 | 90.6 ± 0.9 | 34.2 ± 0.9 | 19.1 ± 2.0 | 18.0 ± 1.1 | 17.2 ± 1.7 |
| 0.01 | 86.7 ± 3.3 | 74.9 ± 2.7 | 28.6 ± 1.4 | 16.4 ± 1.7 | 13.6 ± 1.3 | 18.6 ± 2.1 |
| 0.1 | 78.0 ± 4.2 | 62.0 ± 1.1 | 17.8 ± 1.2 | 10.8 ± 0.6 | 11.4 ± 0.4 | 12.7 ± 0.2 |
| 1 | 68.7 ± 3.4 | 32.5 ± 1.7 | 10.8 ± 0.5 | 5.3 ± 0.5 | 5.3 ± 0.2 | 6.9 ± 0.8 |
| 10 | 63.5 ± 4.2 | 23.6 ± 2.1 | 9.0 ± 0.8 | 5.4 ± 0.4 | 4.5 ± 0.5 | 7.0 ± 0.7 |
| 100 | 64.5 ± 2.7 | 27.8 ± 0.9 | 8.5 ± 0.9 | 5.9 ± 0.4 | 4.1 ± 0.5 | 7.2 ± 1.0 |

(2) (1) Effect on KPK-1 cells

KPK-1 cells (human renal carcinoma cell line) were cultured in accordance with the method of Moore et al. (J. Am. Med. Assoc., 199, 519, 1967) and the resulting cells were washed twice with PBS (−) solution (Nissui Pharmaceutical). Following detachment of the cells with 0.05% trypsin (Flow Laboratories), the cells were pipetted into RPMI-1640 medium (GIBCO Laboratories) to provide a cell suspension. The cells were centrifugally washed at 1200 rpm (25° C.) for 5 minutes (using Hitachi 05PR-22), and resuspended in the same medium, followed by addition of FBS (fetal bovine serum, GIBCO Laboratories) to a final concentration of 10%. After staining the cells with trypan blue solution (Wako Pure Chemicals), the number of viable cells were counted under a light microscope.

It is apparent from Table 2 that against KPK-1 cells, interleukin-1β showed only a very weak growth inhibitory effect, resulting in about 15% inhibition even at a concentraiton of 100 ng/ml. Gamma-interferon caused 57% inhibition at 14 ng/ml. On the other hand, in the group treated with IFN-γ alone, the $ED_{50}$ value of IFN-γ was 11.301 ng/ml. In contrast, in the group wherein 0.1 ng/ml of IL-1β was conjointly used, the $ED_{50}$ value of IFN-γ was 1.862 ng/ml and that in the group wherein 1 ng/ml of IL-1β was conjointly used was 0.255 ng/ml. Thus, a potentiation of growth inhibitory activity by as much as 6.1 to 44.3 times was obtained.

TABLE 2

| IL-1β | Growth of KPK-1 cells (%) | | | | | |
|---|---|---|---|---|---|---|
| | IFN-γ (ng/ml) | | | | | |
| (ng/ml) | 0 | 0.014 | 0.14 | 1.4 | 14 | 140 |
| 0 | 100.0 ± 2.7 | 108.8 ± 5.3 | 99.9 ± 7.2 | 84.4 ± 5.0 | 43.0 ± 1.2 | 12.0 ± 0.9 |
| 0.01 | 119.2 ± 3.3 | 118.3 ± 2.1 | 106.1 ± 2.6 | 87.3 ± 0.7 | 39.2 ± 3.3 | 19.4 ± 2.3 |
| 0.1 | 110.1 ± 3.1 | 112.2 ± 3.4 | 64.4 ± 2.1 | 50.4 ± 4.5 | 22.3 ± 2.3 | 6.5 ± 1.2 |
| 1 | 88.2 ± 3.5 | 84.4 ± 2.1 | 57.3 ± 3.1 | 30.5 ± 2.6 | 5.9 ± 0.9 | 2.3 ± 0.4 |
| 10 | 89.7 ± 4.4 | 84.0 ± 3.2 | 58.1 ± 4.4 | 26.6 ± 2.2 | 5.6 ± 1.6 | 1.7 ± 0.4 |
| 100 | 85.3 ± 4.7 | 77.9 ± 1.2 | 57.8 ± 4.7 | 30.6 ± 1.8 | 8.3 ± 0.6 | 2.4 ± 0.8 |

Using a 12-well microtiter plate (Costar), cell suspensions in a dilution series from $6.3 \times 10^2$ cells/ml to $2 \times 10^4$ cells/ml were placed, in 0.5 ml portions, in the wells and incubated under 5% $CO_2$ at 37° C. for 6 days (Napco $CO_2$ incubator) for a preliminary analysis of cell concentration and incubation time. Then, 0, 0.014, 0.14, 1.4, 14 or 140 ng/ml (i.e. 0, 0.1, 1, 10, 100 and 1000 u/ml) of the gamma-interferon of Reference Example 1 and 0, 0.01, 0.1, 1, 10 or 100 ng/ml of the interleukin-1β of Reference Example 2, in portions of 0.025 ml, were added in various combinations. In addition, 0.5 ml portions of a cell suspension previously adjusted to a concentration of $2 \times 10^4$ cells/ml according to the results of said preliminary analysis were added. The microtiter plate was then incubated under 5% $CO_2$ at 37° C. for 7 days. After the incubation, the cells in the wells were then washed with PBS (+) solution (Nissui Pharmaceutical) and fixed with methanol (Wako Pure Chemicals). After drying in the air, the cells were stained with Giemsa stain (MERCK) and the number of colonies was counted using an automatic particle counter (CP-2000, Shiraimatsu Kikai) or a stereoscopic (3) (1) Effect on various cells SW48 cells (human colon carcinoma cell, Cancer Res., 36, 4562, 1976) were cultured in accordance with the method of Leibovitz et al. (Am. J. Hyg., 78, 173, 1963) and the grown cells were washed twice with PBS (−) solution (Nissui Pharmaceutical). Following detachment of the cells with 0.05% trypsin (Flow Laboratories), the cells were pipetted into L-15 medium (Flow Laboratories) to provide a cell suspension. The cells were centrifugally washed at 1200 rpm (25° C.) for 5 minutes (using Hitachi 05PR-22), and resuspended in the same medium, followed by addition of FBS (fetal bovine serum, GIBCO Laboratories) to a final concentration of 10%. After staining the cells with trypan blue solution (Wako Pure Chemicals), the number of viable cells were counted under a light microscope.

Using a 12-well microtiter plate (Costar), cell suspensions in a dilution series from $6.3 \times 10^2$ cells/ml to $2 \times 10^4$ cells/ml were placed, in 0.5 ml portions, in the wells and incubated under 5% $CO_2$ at 37° C. for 8 days (Napco $CO_2$ incubator) for a preliminary analysis of cell concentration and incubation time. Then, 0 or 1.4 ng/ml of the gamma-interferon of Reference Example 1 and 0 or 1.0 ng/ml of the interleukin-1β of Reference Example 2 were added, in portions of 0.025 ml, either singly or in various combinations. In addition, 0.5 ml portions of a cell suspension previously adjusted to a concentration of $2.5 \times 10^3$ cells/ml according to the results of said preliminary analysis were added. The microtiter plate was then incubated under 5% $CO_2$ at 37° C. for 12 days. After the incubation, the cells in the wells were then washed with PBS (+) solution (Nissui Pharmaceutical) and fixed with methanol (Wako Pure Chemicals).

nor gamma-interferon, used alone, failed to inhibit the growth completely. However, when both agents were used in combination, the growth of Calu-3 cells was substantially completely inhibited. Against KPK-1 and COLO 205 cells, too, the conjoint use of interleukin-1β and gamma-interferon resulted in a significant potentiation of the growth inhibitory effect on these cells just as in the cases set forth in Tables 1 and 2.

TABLE 3

| | Growth of human tumor cells (%) | | | |
|---|---|---|---|---|
| | | % Growth | | |
| Cell line | Control | IL-1β (1 ng/ml) | IFN-γ (1.4 ng/ml) | IL-1β + IFN-γ (1 ng/ml) (1.4 ng/ml) |
| SW48 | 100.0 ± 4.2 | 95.5 ± 3.6 | 101.1 ± 2.0 | 8.3 ± 1.3 |
| KPK-1 | 100.0 ± 3.5 | 161.9 ± 3.9 | 82.6 ± 2.0 | 23.2 ± 1.8 |
| Calu-3 | 100.0 ± 2.1 | 43.4 ± 1.4 | 24.6 ± 1.7 | 1.5 ± 0.8 |
| COLO 205 | 100.0 ± 9.8 | 59.7 ± 3.3 | 20.2 ± 2.2 | 6.5 ± 1.0 |

Calu-3 cells (human lung carcinoma cell, J. Nat. Cancer Inst., 58, 209, 1977) were cultured in accordance with the method of Eagle, H. et al. (Science, 130, 432, 1959) and the resulting cells were washed twice with PBS (−) solution (Nissui Pharmaceutical) and suspended in a medium composed of 0.05% trypsin (Flow Laboratories) plus 10% NEAA (Nonessential amino acid, Flow Laboratories) and containing 1 ml of sodium pyruvate. The cells were centrifugally washed at 1200 rpm (25° C.) for 5 minutes (using Hitachi 05PR-22), and resuspended in the same medium, followed by addition of FCS (GIBCO Laboratories) to a final concentration of 10%. After staining the cells with trypan blue solution (Wako Pure Chemicals), the number of viable cells were counted under a light microscope.

Using a 12-well microtiter plate (Costar), cell suspensions in a dilution series from $6.3 \times 10^2$ cells/ml to $2 \times 10^4$ cells/ml were placed, in 0.5 ml portions, in the wells and incubated under 5% $CO_2$ at 37° C. for 9 days (Napco $CO_2$ incubator) for a preliminary analysis of cell concentration and incubation time. Then, 0 or 1.4 ng/ml of the gamma-interferon of Reference Example 1 and 0 or 1.0 ng/ml of the interleukin-1β of Reference Example 2 were added, in portions of 0.025 ml, either singly or in various combinations. In addition, 0.5 ml portions of a cell suspension previously adjusted to a concentration of $2.0 \times 10^4$ cells/ml according to the results of said preliminary analysis were added. The microtiter plate was then incubated under 5% $CO_2$ at 37° C. for 12 days. The cells in the wells were then washed with PBS (+) solution (Nissui Pharmaceutical) and fixed with methanol (Wako Pure Chemicals).

After conducting the preparation of the COLO 205 and KPK-1 cells as described in Example 1 (1) and (2), respectively, 0 or 1.4 ng/ml of the gamma-interferon of Reference Example 1 and 0 or 1.0 ng/ml of the interleukin-1β of Refernece Example 2 were used singly or in combination to determine the growth inhibitory effects of these antitumor agents on each of the cells.

The results are set forth in Table 3. As for SW 48 cells, neither interleukin-1β nor gamma-interferon inhibited growth when used alone, whereas the use of them in combination achieved growth inhibition of as much as more than 90%. Against Calu-3 cells, too, neither interleukin-1β

Preparation Example 1

| | |
|---|---|
| Interleukin-1β | 0.8 μg/ml |
| Gamma-interferon | 42 μg/ml |
| Tween 80 | 0.01 mg/ml |
| Dextran 40 | 15 mg/ml |
| Cysteine | 0.1 mg/ml |
| HSA (human serum albumin) | 1.0 mg/ml |

The above ingredients were added to 0.01M citric acid-sodium citrate buffer (pH 6.0) to the respective final concentrations indicated above, and the mixture was filtered (using a 0.22 μm membrane filter). The filtrate was aseptically distributed, in 1 ml portions, into vials and lyophilized to provide an injectable preparation of the antitumor agent according to the invention.

For administration, this preparation is dissolved in 1 ml of physiological saline.

Preparation Example 2

| | |
|---|---|
| Interleukin-1β | 0.08 μg/ml |
| Gamma-interferon | 420 μg/ml |
| Tween 80 | 0.01 mg/ml |
| Dextran 40 | 15 mg/ml |
| Cysteine | 0.1 mg/ml |
| HSA (human serum albumin) | 1.0 mg/ml |

The above ingredients were added to 0.01M citric acid-sodium citrate buffer (pH 6.0) to the respective final concentrations indicated above, and the mixture was filtered (using a 0.22 μm membrane filter). The filtrate was aseptically distributed, in 1 ml portions, into vials and lyophilized to provide an injectable preparation of the antitumor agent according to the invention.

For administration, this preparation is dissolved in 1 ml of physiological saline.

We claim:

1. A method of inhibiting tumor growth which consists essentially of administering an anti-tumor effective amount of naturally occurring gamma-interferon and [$Ser^{71}$]

interleukin-1β to a tumor-bearing patient, wherein the tumor is selected from the group consisting of colon adenocarcinoma, renal cancer and lung adenocarcinoma.

2. The method of inhibiting tumor growth which consists essentially of administering an anti-tumor effective amount of naturally occurring gamma-interferon and [Ser$^{71}$] interleukin-1β to a tumor-bearing patient, wherein said anti-tumor effective amount of naturally occurring gamma-interferon is from about 4.2 μg/body/day to 4.2 mg/body/day and said anti-tumor effective amount of [Ser$^{71}$]interleukin-1β is from about 0.08 to 8 μg/body/day, and wherein the tumor is selected from the group consisting of colon adenocarcinoma, renal cancer and lung adenocarcinoma.

* * * * *